United States Patent [19]

Fleigle et al.

[11] Patent Number: 4,505,393
[45] Date of Patent: Mar. 19, 1985

[54] KNOCKED-DOWN EASILY-ASSEMBLED CANNING-LID-STERILIZING RACK

[76] Inventors: David H. Fleigle; Phyllis A. Fleigle, both of R.R. 2, Box 120, Moweaqua, Ill. 62550

[21] Appl. No.: 415,684

[22] Filed: Sep. 7, 1982

[51] Int. Cl.³ .............................................. A47G 19/08
[52] U.S. Cl. .................... 211/41; 229/52 A; 16/114 R; 16/DIG. 24; 294/15; 403/347; 403/252
[58] Field of Search ............... 211/41, 40; 206/200, 206/203, 165, 163, 428, 445; 220/94 R; 229/52 AW, 52 AM, 52 A; 403/347, 252; 16/114 R, DIG. 24, DIG. 15; 294/15

[56] References Cited

U.S. PATENT DOCUMENTS

| | | | |
|---|---|---|---|
| 2,405,914 | 8/1946 | Van Rosen | 229/52 A |
| 2,552,439 | 5/1951 | Lamprecht | 220/94 R X |
| 2,813,633 | 11/1957 | Welling | 211/41 |
| 2,853,224 | 9/1958 | Slater et al. | 229/52 AM X |
| 3,486,631 | 12/1969 | Rodman | 211/41 |
| 3,502,292 | 3/1970 | Yoder | 403/263 X |

FOREIGN PATENT DOCUMENTS

| | | | |
|---|---|---|---|
| 119865 | 10/1947 | Sweden | 211/41 |
| 691621 | 10/1979 | U.S.S.R. | 403/347 |

Primary Examiner—J. Franklin Foss
Assistant Examiner—Blair Johnson
Attorney, Agent, or Firm—Edwin E. Greigg

[57] ABSTRACT

A knocked-down easily-assembled sterilizing rack for holding conventional disk-shaped lids used for sealing mason jars. A sheet-metal inverted-trough-shaped body has a plurality of parallel transaxial slots to hold the lids upright and spaced. An initially unattached bail-shaped handle is dimensioned to embrace the sides and an end of the body for parts-protecting and for economical compact shipping-packaging. The handle and the body have snap-together assembling detent elements.

1 Claim, 6 Drawing Figures

KNOCKED-DOWN EASILY-ASSEMBLED CANNING-LID-STERILIZING RACK

BACKGROUND AND OBJECT OF THE INVENTION

It is broadly old to construct racks for holding various articles in spaced relationships to improve a sterilizing operation. But most racks of this nature are difficult to load, and especially to unload after a heating sterilizing operation. They are also usually large and fragile, making their shipping and storage both expensive and bothersome. It is accordingly the principle object of the present invention to design a canning-lid-sterilizing rack that (1) is easy to load and unload (2) is capable of being very compactly packaged in knocked-down form for economical and damage-proof shipping, and (3) which is very easily and securely snapped-together in assemblage.

BRIEF DESCRIPTIONS OF THE DRAWING FIGURES

DETAILED DESCRIPTION

Figure 1:
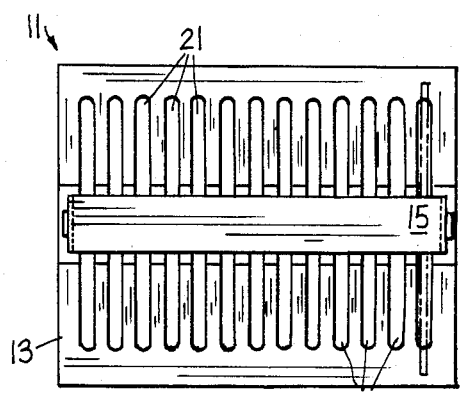
FIG. 1 is a plan view of the assembled rack.
Figure 2:
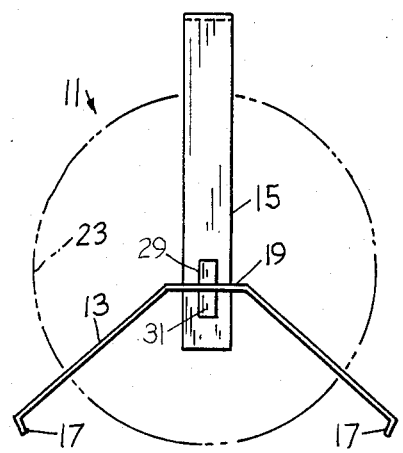
FIG. 2 is an end elevational view of the disclosure of FIG. 1.
Figure 3:
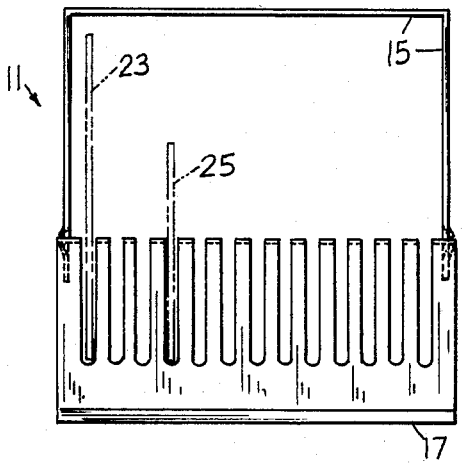
FIG. 3 is a side elevational view of the showing of FIG. 1.

With reference now to the drawings, the numeral 11 generally designates a preferred embodiment of the sterilizing rack, which comprises an inverted trough-shaped base member 13 and a snap-on bail-shaped handle 15. The parts can be made of any corrosion-resistant metal (such as stainless or galvanized steel) or of heat-resistant (e.g. fiber-reinforced) plastic materials.

The base 13 desirably has inwardly turned bottom edges 17, and a flattened crest 19 for reasons hereinafter explained. The base 13 has a plurality of parallel slots 21 cut therein and sized to hold either of the two common sizes of jar-lids 23 (large) and 25 (small), which are easily removed, while still hot, as by common kitchen-type tongs (not shown).

Figure 4:
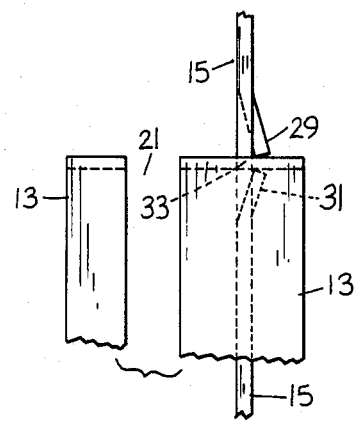
FIG. 4 is an enlarged fragmentary view of the central portion of the right margin of FIG. 3.

The bail-shaped handle 15 is shown as having a pair of struck-out tongues 29 and 31 which lock the handle 15 assembled with the base 13 when the bail ends are inserted downwardly through slits 33 (FIG. 5) in the ends of the crest 19. The bottom tongues 31 yieldably cam past the outer lips of the slits 33 and then expand outwardly to lock under the crest 19 while the upper tongues 29 lock against the upper crest surface (FIG. 4).

Figure 5:
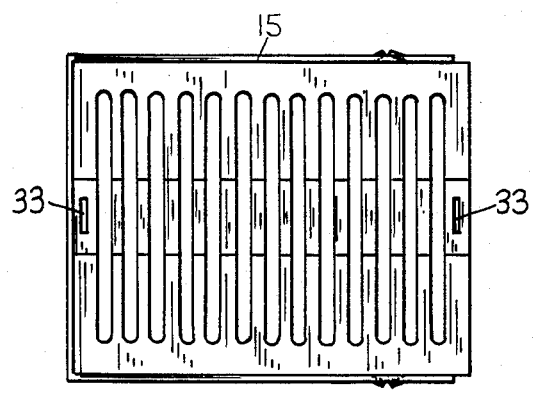
FIG. 5 is a plan view of the unassembled rack parts nested for safe and economical compact packaging.
Figure 6:
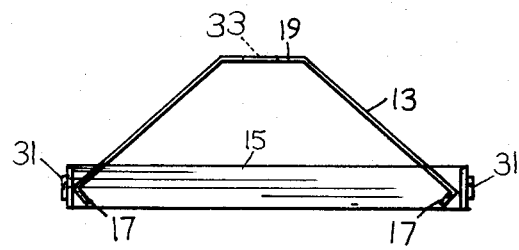
FIG. 6 is an end elevational view of the nested-parts shown in FIG. 5 as seen from the right side of FIG. 5.

An important feature of the disclosure resides in shaping the bail 15 to closely embrace the periphery of the base 13, as shown in FIGS. 5 and 6. This permits economical parts-protecting and space-saving compact-packaging of the knocked-down rack.

The invention having been described, what is claimed is:

1. A sterilizing rack for holding a plurality of conventional canning-lids, comprising: an inverted one-piece trough-shaped sheet-material body having a plurality of spaced parallel trans-axial slots therein of a shape and size to hold large and/or small conventional canning lids therein, spaced from each other and from a rack-supporting horizontal surface; said trough-shape defining a crest thereon, wherein said body includes slits at its opposite ends in the area of said crest, each of said slits including opposed edges and, a bail-shaped handle overlying said body and fixed at its extremities to the ends of the crest of said inverted trough-shaped body, said bail-shaped handle being U-shaped and embracing the sides and one end of said body, and having a pair of oppositely disposed struck-out tongues adjacent each of its ends in snap-together handle-locking engagement with said edges of the respective slits adjacent said slit being received between said respective pair of tongues.

* * * * *